United States Patent [19]

Heiba et al.

[11] 4,011,239

[45] Mar. 8, 1977

[54] SELECTIVE REACTIONS OF FREE RADICALS WITH OLEFINS IN THE PRESENCE OF AN ION OF Mn, V, OR Ce

[75] Inventors: El Ahmadi I. Heiba, Princeton; Ralph M. Dessau, Highland Park, both of N.J.

[73] Assignee: Mobil Oil Corporation, New York, N.Y.

[22] Filed: Sept. 24, 1973

[21] Appl. No.: 400,484

Related U.S. Application Data

[63] Continuation-in-part of Ser. No. 755,732, Aug. 27, 1968, abandoned, and a continuation-in-part of Ser. No. 714,447, March 20, 1968, abandoned.

[52] U.S. Cl. .................. 260/327 S; 260/346.1 R; 260/346.2 R; 260/347.3; 260/347.5; 260/347.8; 260/456 R; 260/465.3; 260/483; 260/484 A; 260/486 R; 260/497 R; 260/586 C; 260/595; 260/597 R; 260/607 AL; 260/609 B; 260/644

[51] Int. Cl.$^2$ ............... C07D 327/04; C07C 69/52; C07C 45/02

[58] Field of Search ........ 260/497 R, 327 S, 609 B, 260/586 C, 595, 597 R, 483, 484 A, 486 R, 465.3, 456 R, 607 AL, 644, 346.1 R, 346.2 R, 347.3, 347.5, 347.8

[56] References Cited

FOREIGN PATENTS OR APPLICATIONS 218,145  5/1968  U.S.S.R.

OTHER PUBLICATIONS

Heiba, et al., JACS vol. 90:4, Feb. 14, 1968, p. 1082–1084.
Van Helden et al., Chem. Abstr. vol. 55, (1961), 17564i–17565b.

*Primary Examiner*—Henry R. Jiles
*Assistant Examiner*—Bernard Dentz
*Attorney, Agent, or Firm*—Charles A. Huggett; Vincent J. Frilette

[57] ABSTRACT

An olefin is reacted with a source of X free radical in the presence of an ion of manganese, vanadium, or cerium having a valence higher than the lowest valence above the zero valent form of the metal to form derivatives of the olefin that contain one or more functional groups. The free radical X is one that is resistant to substantial oxidation by the ion of the metal and is obtained from ketones, aldehydes, esters, nitriles, nitroparaffins, sulfoxides, thiosulfonic acid esters, alkanesulfonic acids, alkanesulfinic acids, and thiols.

58 Claims, No Drawings

SELECTIVE REACTIONS OF FREE RADICALS WITH OLEFINS IN THE PRESENCE OF AN ION OF MN, V, OR CE

CROSS REFERENCE TO RELATED APPLICATIONS

This application is a continuation-in-part of our copending application Ser. No. 755,732, filed Aug. 27, 1968 and now abandoned. This latter application was a continuation-in-part of our then copending application Ser. No. 714,447, filed Mar. 20, 1968 and now abandoned.

BACKGROUND OF THE INVENTION

1. Field of the Invention

This invention relates to a method for the selective reaction of free radicals with an olefin.

2. Description of the Prior Art

It is believed that the reaction of a free radical derived from the compounds mentioned in the presence of an ion of manganese, vanadium, or cerium in the valence state mentioned in novel.

SUMMARY OF THE INVENTION

In accordance with the invention of olefin is reacted with a source of ·X free radical in the presence of an ion of manganese, vanadium, or cerium having a valence higher than the lowest valence above the zero valent form of the metal, the free radicals being obtained from ketones, aldehydes, esters, nitriles, nitroparaffins, sulfoxides, thiosulfonic acid esters, alkanesulfonic acids, alkanesulfinic acids, and thiols.

DESCRIPTION OF THE PREFERRED EMBODIMENTS

The ·X free radical reacted with the compound having olefinic unsaturation is one selected from the following classes:

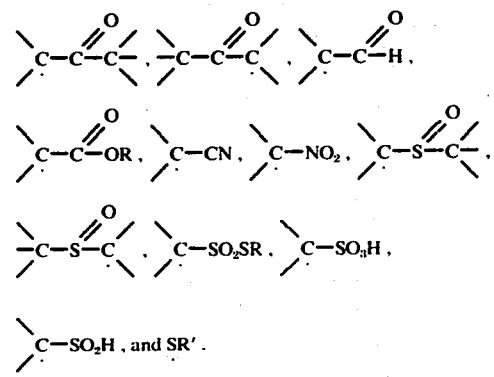

These free radicals are derived respectively from a ketone, a ketone, an aldehyde, an ester, a nitrile, a nitroparaffin, a sulfoxide, a sulfoxide, a thiosulfonic acid ester, an alkanesulfonic acid, an alkanesulfinic acid, and a thiol.

In the free radicals above, the dangling valences may be satisfied by a wide variety of groups. R is generally an alkyl group. R' is generally a hydrocarbyl or substituted hydrocarbyl group. The method is capable of providing high yields of valuable products containing the moiety

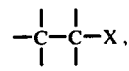

where X is one of the radicals just defined.

It may be helpful to set forth the reaction sequences and the types of products obtained with the ketone-derived radical

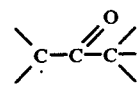

The reaction sequences and the types of products obtained depend upon the type of olefin employed. Where the olefin contains substituents consisting solely of hydrogen or hydrocarbyl radicals, the reaction sequences and the types of products obtained are different than those obtained where the olefin contains a substituent which may be a group, herein designated as a functional group to which further reference will be made hereinafter.

There will be first illustrated the reaction sequence and the types of products obtained where the olefin consists solely of hydrogen or hydrocarbyl radicals. These will be set forth in equation form and the olefin will be designated as R''CH=CH$_2$, R'' being hydrogen or a hydrocarbyl group. Further, Mn$^{+++}$ will be used as the metal ion, manganic acetate as the source of the Mn$^{+++}$,

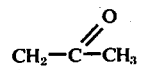

as the specific free radical, and acetone as the ketone from which the specific free radical is derived.

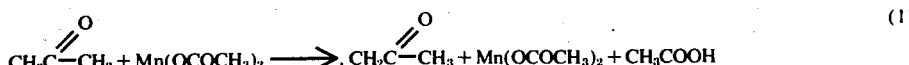

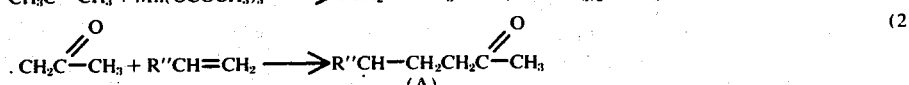

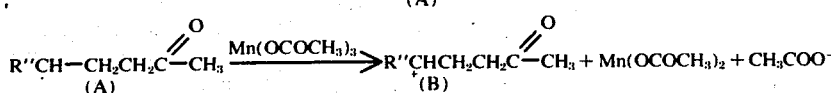

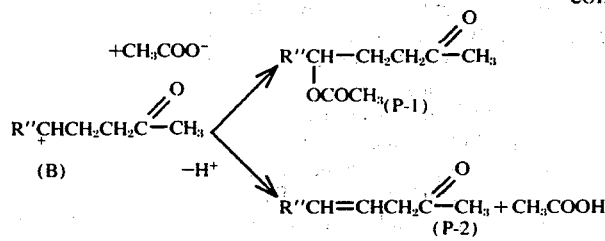

As shown in equation (1), the

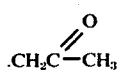

free radical is produced when manganic acetate, dissolved in acetic acid, is heated with acetone. According to the reaction of equation (2), the reactive acetylmethyl free radical,

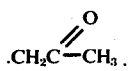

adds to the double bond of the olefin, forming the free radical (A). In equation (3), oxidation of free radical intermediate (A) occurs in the presence of manganic acetate to form the cation intermediate (B), with reduction of $Mn^{+3}$ to $Mn^{+2}$ and formation of an acetate ion. In equation (4), the cation (B) reacts with the acetate ion to form the keto-ester product (P-1), about 90% of the $Mn^{+3}$ consumed forming this product; and in equation (5) about 10% of the $Mn^{+3}$ consumed forms the beta-gamma unsaturated ketone product (P-2) by losing H. If R" is hydrogen, the product (P-1) is 1-acetoxy-pentanone-4, and (P-2) is 1-penten-4-one. It is pointed out that the acetylmethyl free radical is not substantially oxidized by $Mn^{+3}$, but the free radical intermediate (A) is readily oxidized, thus providing a case of selective oxidation. In other words, (A) has a lower ionization potential than the acetylmethyl radical. The ion intermediate (B) may react in either of two ways, as shown in equations (4) and (5).

It is of interest to note that when R" of the olefin R"CH=CH$_2$ is aryl, the unsaturated ketone product (P-2) is not obtained, rather, a heterocyclic ring-containing product (P-3) is formed according to the following equation:

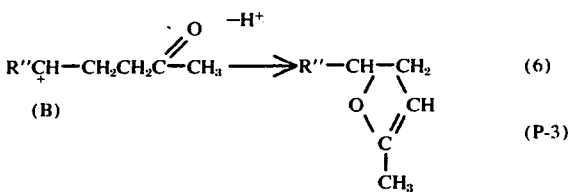

The product (P-3), with R" equal to aryl, is an aryl-substituted dihydrofuran, obtained in a yield of 10 to 20% of the $Mn^{+3}$ consumed. It will be understood that equations (1) through (4) are applicable, and that equation (6) takes the place of equation (5). As an example, if R" is phenyl, product (P-3) is 1-phenyl-4-methyl-dihydrofuran, and product (P-1) is 1-acetoxy-1-phenyl-pentanone-4, the latter obtained in 80-90% yield, basis noted.

As may be seen from equations (1) through (6), the structure

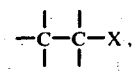

which broadly characterizes the products of the invention, may be in the form of a linear chain, as in products (P-1) and (P-2), or in the form of a cyclic moiety, as in product (P-3).

Dihydrofuran derivatives are also obtainable by the process of the invention employing, as reactants, cyclic and non-cyclic diketones, for example, cyclic and non-cyclic 1,3-diketones such as 1,3-cyclohexanedione and 2,4-pentanedione, and olefins. When employing a diketone, the olefin need not be an aryl-substituted olefin in order to obtain dihydrofuran. The dihydrofuran derivatives can also be obtained by the process of the invention employing, as reactants, beta-keto-esters, beta-keto-nitriles, and beta-keto-amides and olefins. Ketonic dihydrofuran structures including the following can be obtained:

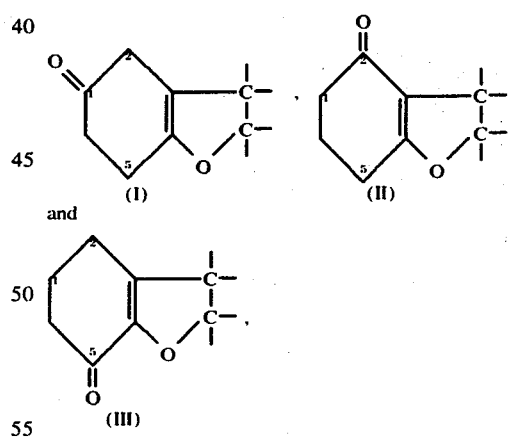

the dangling valences being satisfied with hydrogen or with a hydrocarbyl group such as an alkyl, aryl, aralkyl, or alkaryl group.

The $Mm^{+2}$ compound, note equations (1) and (3), is recoverable as manganous acetate, but as described below, it is feasible to regenerate $Mn^{+3}$ from it. The high yields of product indicate a high selectivity of addition of the acetylmethyl free radical to the double bond of the olefin.

There will now be illustrated in equation form the reaction sequence and the products obtained where the olefin contains an ether or ester group as a substituent.

In this illustration, Mn$^{+++}$ will be used as the metal ion,

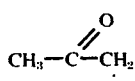

as the specific free radical, and acetone as the ketone from which the specific free radical is derived. The olefin will be isopropenyl acetate,

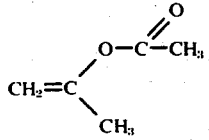

the functional group being

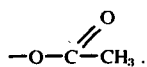

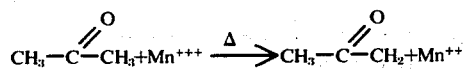 (7)

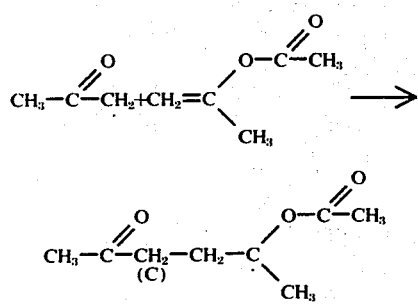 (8)

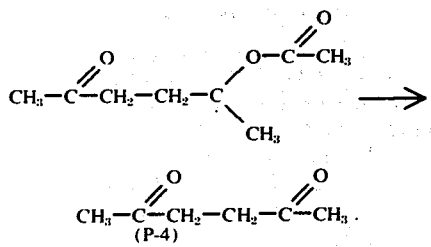 (9)

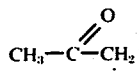
(P-4)

As shown in equation (7), the

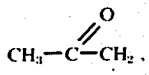

free radical is produced when the manganic ion is heated with acetone. According to the reaction of equation (8), the reactive acetylmethyl free radical,

adds to the double bond of the isopropenyl acetate, forming the free radical (C). In equation (9), elimination of the free radical,

occurs with the formation of product (P-4), hexane-2,5 dione.

The reaction sequence of equations (7) to (9) may be generalized as follows:

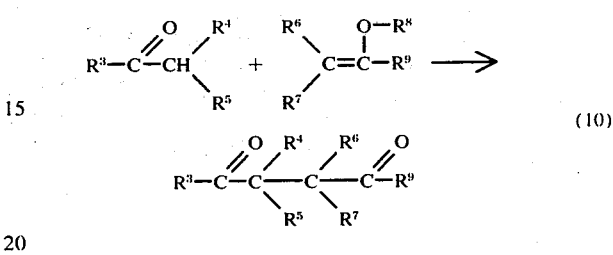 (10)

In equation (10), R$^8$ can be an alkyl, aryl, acyl, or aroyl group. R$^3$ to R$^7$ and R$^9$ may be hydrogen or a hydrocarbyl group. It will thus be seen that the reaction of equation (10) will apply where the olefin is an unsaturated ester or ether, i.e., an enol ester or an enol ether.

A similar type of reaction mechanism involving elimination of a free radical occurs where the olefin is a chloride or a sulfide. Thus, taking cyclohexanone as the ketone and allylic chloride as the olefin, the reaction is as follows:

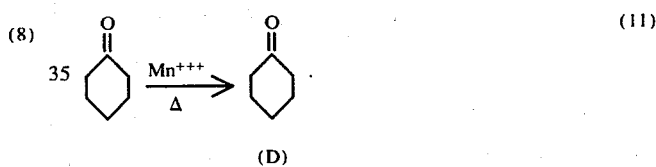 (11)

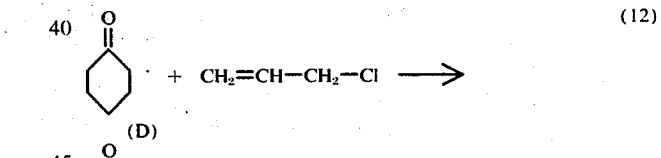 (12)

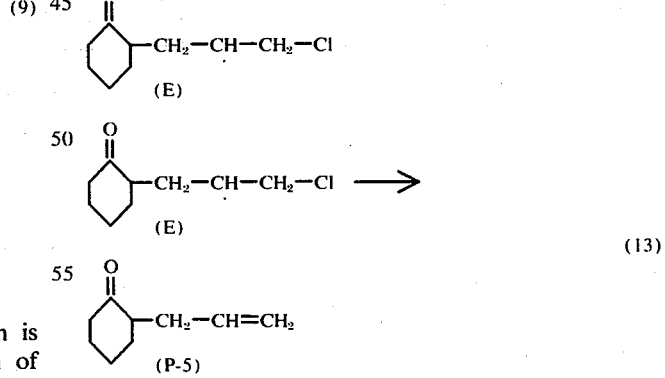 (13)

As shown in equation (11), the free radical (D) is produced when the manganic ion is heated with cyclohexanone. According to the reaction of equation (12), the free radical (D) adds to the double bond of the allylic chloride forming the free radical (E). In equation (13), elimination of the radical, Cl·, occurs with the formation of the product (P-5), 2-allyl cyclohexanone.

Where the free radical is the aldehyde-derived radical,

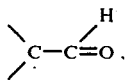

and the substituents on the olefin are hydrogen or hydrocarbyl groups, the reaction parallel those of equations (1) through (6). Thus, if the aldehyde is acetaldehyde, the free radical derived from it is formylmethyl, ·CH$_2$CHO, and equation (1) can be written to correspond to these changes. The free radical, ·CH$_2$CHO, in reactions corresponding to equations (1), (3), (4), and (5), adds to the olefin R″CH═CH$_2$ giving an aldehyde-ester product,

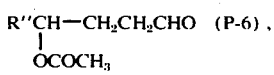

corresponding to product (P-1), and an unsaturated product, R CH═CHCH$_2$CHO (P-7), corresponding to (P-2). If R″ is hydrogen, the aldehyde-ester product is 1-acetoxy-butanal-4, and the unsaturated aldehyde product is buten-1-al-3. Similarly, if R″ is aryl, the last-mentioned product is not obtained, rather, a heterocyclic ring-containing product is formed; thus, the reaction, paralleling equation (6), may be written:

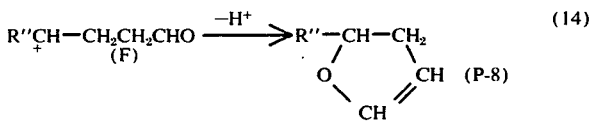

showing the ion intermediate (F) reacting to form the product (P-8), an aryl-substituted dihydrofuran. If R″ in equation (14) is phyenyl, (P-8) is 1-phenyl-dihydrofuran.

Where the free radical is the aldehyde-derived radical and the substituents on the olefin are functional groups, the reactions parallel those of equations (7) through (9) and equation (10). Thus, if the aldehyde is acetaldehyde and the olefin is isopropenyl acetate, the product will be

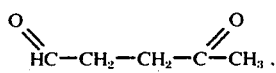

1-acetoxy-butanal-4. Accordingly, a keto-aldehyde can be formed by the reaction of the free radical derived from an aldehyde with an enol ester. The enol ester may be a vinyl ester. A keto-aldehyde can also be formed by the reaction of the free radical derived from an aldehyde with an anol ether, such as a vinyl ether.

With an ester-derived free radical,

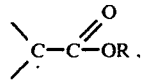

the reactions again parallel those of equations (1) through (5). Using methyl acetate,

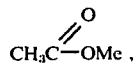

as the starting ester, the resulting free radical is methyl carboxyl methyl,

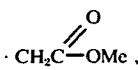

obtainable by a reaction corresponding to equation (1). By reactions corresponding to equations (2) through (5), this radical adds to the olefin R″CH═CH$_2$ giving a diester product,

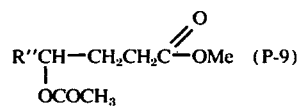

and an unsaturated ester

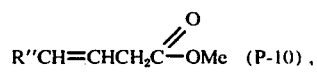

corresponding respectively to (P-1) and (P-2). If R″ is hydrogen, then (P-9) is the methyl ester of 4-acetoxybutanoic acid, and (P-10) is the methyl ester of buten-4-oic acid. In this case, however, if R″ is aryl, no cyclization takes place; the equations corresponding to (4) and (5) are as follows:

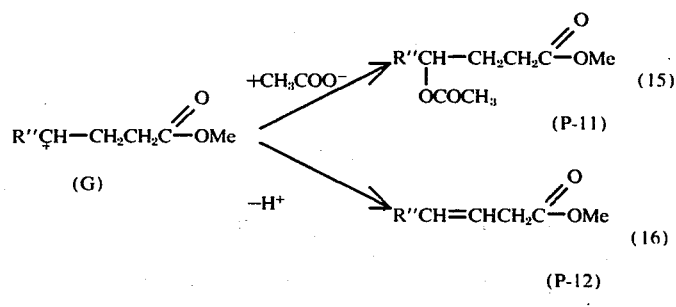

The ion intermediate (G) forms products (P-11) and (P-12). If R″ in equations (15) and (16) is phenyl, product (P-11) is the methyl ester of 4-phenyl-4-acetoxy-butanoic acid and (P-12) is the methyl ester of 4-phenyl-buten-4-oic acid.

Where the free radical is the ester-derived radical and the substituents on the olefin are ether and ester groups, the reactions parallel those of equations (7) through (9) and equation (10). Thus, if the ester is methyl acetate and the olefin is isopropenyl acetate, the product will be

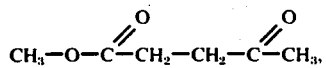

a keto-ester. Accordingly, a keto-ester can be formed by the reaction of the free radical derived from an ester with an enol ester. The enol ester may be a vinyl ester. A keto-ester can also be formed by the reaction of the free radical derived from an ester with an enol ether, such as a vinyl ether.

When the free radical is derived from a nitrile, as with

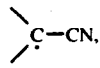

and regardless of the substituents on the olefin, the reactions correspond to equations (1) through (5). Thus, starting with methyl nitrile, $CH_3CN$, the free radical is cyanomethyl, $\cdot CH_2CN$, and is obtained by a reaction corresponding to equation (1). This radical adds to the olefin $R''CH=CH_2$, as in the case of equations (2) through (5), giving a cyano-ester product,

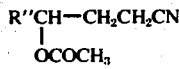 (P-13)

and an unsaturated nitrile, $R''CH=CHCH_2CN$ (P-14). If R'' is hydrogen, (P-13) is 1-acetoxy-butyronitrile-4 and (P-14) is buten-4-nitrile-1. If R'' is aryl, the reactions correspond to equations (12) and (13), i.e., no cyclization occurs, and the products are

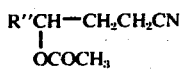 (P-15)

and $R''CH=CHCH_2CN$ (P-16). If R'' is phenyl, (P-15) is 4-phenyl-4-acetoxy-butyronitrile and (P-16) is 4-phenyl-buten-4-nitrile-1.

In the case of a sulfoxide-derived free radical,

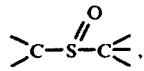

and regardless of the substituents on the olefin, the reactions again correspond to equations (1) through (5). Starting for example with dimethyl sulfoxide,

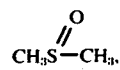

the free radical is sulfoxymethyl,

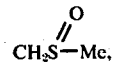

obtained in a manner corresponding to equation (1), and this radical adds to the olefin $R''CH=CH_2$ in steps corresponding to equations (2) through (5), giving an acetoxy-substituted dialkyl sulfoxide,

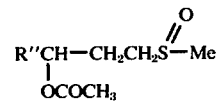 (P-17)

and an alkyl alkenyl sulfoxide,

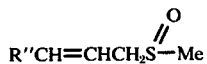 (P-18).

If R'' is hydrogen, (P-17) is 3-acetoxy(n-propyl)-methyl sulfoxide and (P-18) is methyl-beta-propenyl sulfoxide. When R'' is an aryl group, no cyclization occurs, the products corresponding to those where the free radical is derived from an ester or a nitrile.

With a nitroparaffin-derived free radical, $<C-NO_2$, and regardless of the substituents on the olefin, the reactions parallel equations (1) through (5). Using nitromethane, $CH_3NO_2$, as the starting reactant, the radical derived from it is nitromethyl, $\cdot CH_2-NO_2$, and by addition to the olefin reactant this forms an acetoxy-substituted nitropropane,

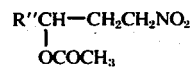 (P-19)

and a nitroalkene, $R''CH=CHCH_2NO_2$ (P-20). If R'' is hydrogen, (P-19) is 1-acetoxy-3-nitropropane and (P-20) is 1-nitropropene. When R'' is aryl, no cyclization takes place; and if R'' is phenyl, (P-19) is 1-acetoxy-1-phenyl-3-nitropropane and (P-20) is alpha-nitromethyl-styrene.

A thiosulfonic acid ester free radical,

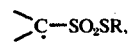

regardless of the substituents on the olefin, undergoes reactions corresponding to equations (1) through (5). For example, the methyl ester of methanethiosulfonic acid, $CH_3SO_2SCH_3$, gives thiosulfonic acid methyl ester free radical, $\cdot CH_2SO_2SCH_3$, which adds to the olefin reactant to form an acetoxy-substituted alkyl thiosulfonic acid ester,

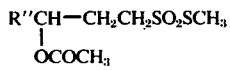 (P-21)

and an alkenethiosulfonic acid alkyl ester, $R'\lambda'CH=CHCH_2SO_2SCH_3$ (P-22). If R'' is hydrogen, (P-21) is the methyl ester of 3-acetoxy-n-propyl-thiosulfonic acid, and (P-22) is the methyl ester of beta-propenethiosulfonic acid.

The radical, >C-SO₃H, derived from an alkanesulfonic acid RSO₃H, regardless of the substituents on the olefin, reacts in a way corresponding to equations (1), (2), and (3). Thus, starting with methanesulfonic acid, the radical produced is methylsulfonic acid free radical, ·CH₂SO₃H, and this adds to the starting olefin to form the ion intermediate R″ĊH-CH₂CH₂SO₃H, corresponding to the intermediate product (B) of equation (3). Then the following reaction occurs:

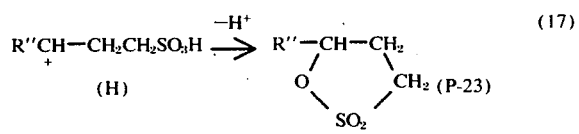 (17)

The ion intermediate (H) loses a hydrogen ion to form product (P-23), sultone; if R″ is hydrogen, (P-23) is 3-hydroxy-1-propanesulfonic acid sultone, and if R″ is phenyl, the product is 3-phenyl-3-hydroxy-1-propanesulfonic acid sultone.

The radical, >C-SO₂H, derived from an alkanesulfinic acid, regardless of the substituents on the olefin, RSO₂H, reacts like the radical, >C-SO₃H, just described. Starting with methanesulfinic acid, CH₃SO₂H, there is formed the methylsulfinic acid free radical, ·CH₂SO₂H, which adds to the starting olefin to form a sulfolane product,

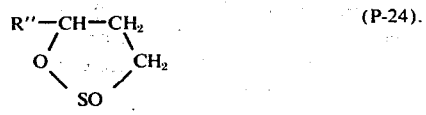 (P-24).

If R″ is methyl, the product is 1-methylsulfolane.

Finally, where the free radical is derived from a thiol, R′SH, regardless of the substituents on the olefin, the following reactions take place, using R′SH as the starting thiol:

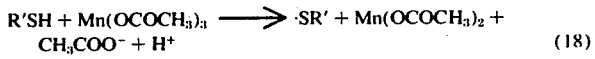 (18)

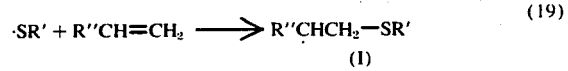 (19)

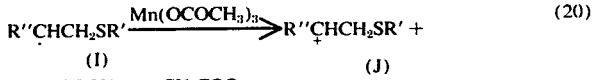 (20)

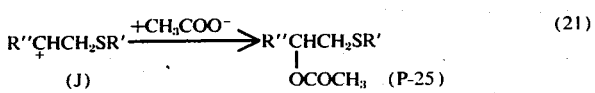 (21)

 (22)

According to equation (18), the thiyl free radical, ·SR′, forms and adds to the double bond of the olefin (equation (19)) to form the free radical intermediate (I). The latter forms the ion intermediate (J) by equation (20). Intermediate (J) reacts by equation (21) to form about 90% of a 1-ester-2-thio compound (P-25) or by equation (22) to form about 10% of a vinyl sulfide (P-26). If R″ is hydrogen and R′ is methyl, product (P-25) is 1-acetoxy-2-methylthioethane and (P-26) is methylvinylsulfide. In carrying out this olefin-thiol sequence, it is preferred to supply the thiol in slow or dropwise fashion to the olefin- and manganese acetate-containing mixture in order to avoid any chemical addition of R′SH to the radical intermediate (I) in equation (20).

In each of the foregoing reaction sequences, it is apparent that the free radical intermediate, such as at (A) in equation (2), is readily oxidized by the Mn⁺³, whereas the free radical ·X, such as the acetylmethyl radical in equation (1), is not; or to put it another way, the former radical has a lower ionization potential than ·X.

The olefin may be broadly defined as

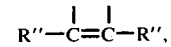

with both of R″ being equal to hydrogen, a hydrocarbyl group, or an organyl group, and with one R″ being the same as or different from the other R″. The term "hydrocarbyl" designates any group containing only carbon and hydrogen, such as alkyl, alkenyl, alkynyl, aryl, alkaryl, aralkyl, etc., and the term "organyl" designates hydrocarbyl and heterocyclic groups. Suitable illustrative olefins include ethylene, propylene, the butenes, pentenes, hexenes, heptenes, octenes, nonenes, decenes, undecenes, dodecenes, tetradecenes, pentadecenes, hexadecenes, octadecenes, eicosenes, hexacosenes, triacontenes, etc. These may be straight or branched chain olefins with the double bond in the 1-position or any other position. Olefin oligomers are useful, such as propylene tetramer, isobutylene trimer, propylene pentamer, isobutylene tetramer, propylene hexamer, etc. Also suitable are open chain, conjugated or unconjugated diolefins having 3 to 20 or 30 or more carbons, and including allene, butadiene, isoprene, pentadiene, hexadiene, heptadiene, diisobutenyl, decadiene, and the like; also substituted diolefins like 2-cyanobutadiene, and chloroprene. Also of use are open chain olefins having more than two double bonds, sometimes designated oligo-olefins, such as hexatriene, 2,6-dimethyl-2,4,6-octatriene, etc. Cyclic olefins are suitable, such as cyclopentene, cyclohexene, cycloheptene, cyclooctene, and terpenes such as the various menthenes, thujenes, carenes, pinenes, and bornylenes; also cyclic diolefins and cyclic oligo-olefins like cyclobutadiene, cyclopentadiene, fulvene, norbornadiene, cyclooctadiene, 4-vinylcyclohexene, limonene, dipentene, dicyclopentadiene, cycloheptatriene, cyclooctatriene, bicyclo(2.2.2)octa-2,5,7-triene, cyclonona-1,4,7-triene, cyclooctatetraene, and the like. Olefins having both double and triple bonds are of value, such as butenyne, 1,6-heptadiene-3-yne, 3,6-dimethyl-2,6-octadiene-4-yne, 1,7-octaenyne, etc.

It will be seen that nearly all of the foregoing compounds are hydrocarbons having one, two or more double bonds and having an open chain or a cyclic structure.

Other useful olefins are those of the formula,

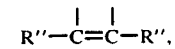

wherein one or both of R″ may be a group, herein designated a functional group, such as acyl, acyloxy, alkoxy, aldehyde —CHO or alkyl aldehyde RCHO, alkylmercapto RS—, amide —CONH₂ or alkyl amide —RCONH₂, alkenylmercapto RCH=CHS—, aryloxy, aroyl, aroyloxy, arylmercapto, aralkylmercapto, alkarylmercapto, carboxy, alkyl carboxy —RCOOH, alkenyl carboxy RCH=CHCOOH, cyano, alkyl cyano —RCN, alkenyl cyano, halogen like Cl, Br, and F, isocyano, nitro, various heterocyclic radicals like pyridyl and substituted pyridyl, quinolyl, isoquinolyl, acridyl, pyridazinyl, pyrimidyl, pyrazinyl, pyrazolyl, pyrrolyl, furyl, indolyl, imidazolyl, oxazolyl, thiazolyl, etc. and including substituted heterocyclic radicals of the foregoing description.

It will be apparent that many of the foregoing R″ groups may, for convenience, be classified as hydrocarbyl-containing groups, and this definition may include hydrocarbyl groups and groups containing carbon and hydrogen and at least one other atom. The dangling valences in the expression,

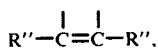

may be satisfied by any suitable groups selected from the foregoing radicals, such as hydrogen, alkyl, alkenyl, aryl, or any of the groups noted above represented by R″.

Examples of some of these olefins may be listed, as where one R″ is one of the foregoing functional groups, while the other R″ may be hydrogen, hydrocarbyl, or organyl, or even one of the said foregoing functional groups in which case it may be the same as or different from the other R″. Thus, in the following table, a value for R″ is listed and opposite it are illustrative examples of the olefin.

TABLE I

| R″ | Olefin |
|---|---|
| Acyl | Unsaturated ketone like methyl vinyl ketone, dodecyl vinyl ketone, mesityl oxide, phorone, isophorone, cyclohexenone, acrylophenone, etc. |
| Acyloxy | Unsaturated ester like vinyl acetate, allyl acetate, cinnamyl acetate, vinyl stearate, crotyl butyrate, methallyl propionate, butyl acrylate, octyl acrylate, octadecyl methacrylate, etc. |
| Alkoxy | Unsaturated ether like vinyl ethyl ether, 1-butenyl ethyl ether, divinyl ether, benzyl vinyl ether, 2-methoxy-1-hexene, 2-butoxy-2-octene, etc. |
| Aldehyde or Alkyl Aldehyde | Unsaturated aldehyde like acrolein, methacrolein, crotonaldehyde, citronellal, citral, butenedial, 2-pentenal, 2-heptenal, 2-octenal, 2-decenal, 2,4-decadienal, 3-phenyl-2-propenal, alpha-cyclohexyl-acrolein, etc. |
| Alkylmercapto | Alkyl alkenyl sulfide such as allyl methyl sulfide, vinyl ethyl sulfide, vinyl cetyl sulfide, divinyl sulfide, etc. |
| Amide or Alkyl Amide | Unsaturated amide like acrylamide, methacrylamide, aconitamide, N-phenylmethyl-acrylamide, N-beta-vinyloxy-ethylformamide, etc. |
| Aryloxy | Unsaturated aryl ether like vinyl phenyl ether, vinyl tolyl ether, etc. |
| Aroyl | Unsaturated aryl ketone like vinyl phenyl ketone, allyl xylyl ketone, etc. |
| Aroyloxy | Unsaturated aromatic ester like alkyl benzoate, etc. |

TABLE I-continued

| R″ | Olefin |
|---|---|
| Arylmercapto | Unsaturated aryl sulfide like vinyl phenyl sulfide, vinyl 1-naphthyl sulfide, etc. |
| Carboxy or Alkyl Carboxy | Unsaturated acid like maleic, chlormaleic, fumaric, crotonic, isocrotonic, itaconic, citraconic, acrylic, cyano-acrylic, phenylacrylic, methacrylic, methoxyacrylic, vinylacrylic, ethylacrylic, beta-pentenoic, angelic, tiglic, hydrosorbic, 3-octenoic, 10-undecenoic, 7,9-dodecadienoic, lauroleic, oleic, elaidic, linoleic, linolenic, 10,12-eicosadienoic, beta-chloracrylic, beta-chlorcrotonic, etc. Also the anhydrides of these various acids. |
| Nitrile or Alkyl Nitrile | Unsaturated nitrile like acrylonitrile, methacrylonitrile, alpha-butyl acrylonitrile, beta-phenyl acrylonitrile, crotonitrile, oleonitrile, 2-cyano-3-heptenoic acid, beta-propenonitrile, undecylenonitrile, etc. |
| Halogen | Unsaturated halogenated compound like tricloroethane, tetrachlorethene, allyl fluoride, the trichloropropenes, crotyl chloride, n-pentenyl bromide, chloroprene, etc. |
| Thiol or Alkyl Thiol | Unsaturated mercaptan like vinyl mercaptan, allyl mercaptan, etc. |
| Isocyanide | Unsaturated isocyanide like allyl isocyanide, crotonyl isocyanide, etc. |
| Nitro | Unsaturated nitro compound like beta-nitrostyrene, nitroethylene, chloronitrostyrene, etc. |
| Heterocyclic | Unsaturated compound like the vinylquinolines, vinylpyrrolidones, vinyl pyridines, 2-styryl-furan, 2-furanacrylic acid, and the like. |

The olefin,

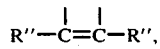

may have any suitable molecular weight, but it is of interest to note that compounds of fairly high molecular weight, having up to 80 or 90 or more carbon atoms, may be reacted. On the lower end, compounds having as low as two carbons, such as ethylene, may be reacted. The olefin may be normally gaseous, or liquid, or solid, and solvents may be employed to dissolve it prior to reaction. In the case of some liquid olefins, they may themselves act as solvents for the manganese compound and the free radical source.

Considering again the free radical, X, this may be a species of any of the broadly defined free radicals noted above and listed, for convenience, in the following table.

TABLE II

| No. | Free Radical |
|---|---|
| 1 | ![structure] |

TABLE II-continued

| No. | Free Radical |
|---|---|
| II | $\diagdown_{\diagup}\!C\!-\!C\overset{\displaystyle O}{=}\!C\diagup^{\diagdown}$ |
| III | $\diagdown_{\diagup}\!C\!-\!C\overset{\displaystyle H}{=}\!O$ |
| IV | $\diagdown_{\diagup}\!C\!-\!C\overset{\displaystyle O}{=}\!OR$ |
| V | $\diagdown_{\diagup}\!C\!-\!CN$ |
| VI | $\diagdown_{\diagup}\!C\!-\!S\overset{\displaystyle O}{=}\!C\diagup^{\diagdown}$ |
| VII | $\diagdown_{\diagup}\!C\!-\!S\overset{\displaystyle O}{=}\!C\diagup^{\diagdown}$ |
| VIII | $\diagdown_{\diagup}\!C\!-\!NO_2$ |
| IX | $\diagdown_{\diagup}\!C\!-\!SO_2SR$ |
| X | $\diagdown_{\diagup}\!C\!-\!SO_3H$ |
| XI | $\diagdown_{\diagup}\!C\!-\!SO_2H$ |
| XII | $\cdot SR'$ |

Nos. I through IV are carbonyl-containing radicals; No. V is a cyano-containing radical; Nos. VI, VII, IX, X, XI, and XII are sulfur-containing radicals, and No. VIII is a nitro-containing radical. Nos. VI, VII, IX, X, and XI are also oxy-sulfur-substituted methyl radicals, and Nos. V and VIII are nitrogen-containing radicals. The ensuing remarks will refer by number to the various radicals listed in Table II.

The ketone-derived radical, No. I, may be formed from an enolizable ketone, or radical precursor, which may be broadly represented as

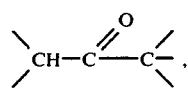

and included by this formula are such specific enolizable ketones as isopropyl methyl ketone, $$\text{Me}\diagdown_{\text{Me}\diagup}\!CH\!-\!C\overset{\displaystyle O}{=}\!C\diagup\!-\!H\diagdown_{H}$$

methyl n-propyl ketone, $$\text{Et}\diagdown_{H\diagup}\!CH\!-\!C\overset{\displaystyle O}{=}\!C\diagup\!-\!H\diagdown_{H}$$

acetophenone, $$H\diagdown_{H\diagup}\!CH\!-\!C\overset{\displaystyle O}{=}\!Ph$$

acetone, $$H\diagdown_{H\diagup}\!CH\!-\!C\overset{\displaystyle O}{=}\!C\diagup\!-\!H\diagdown_{H}$$

cyclohexanone, etc.

A preferred method (for convenience, designated the manganic acetate/acetic acid method) of producing radical No. I is to dissolve the higher-valent reducible metal compound, such as a manganic compound, in a polar solvent like acetic acid, in the presence of a radical precursor compound at a temperature ranging up to the boiling point of the solution, preferably from 40° C. to the boiling point. Temperatures above boiling may be used if pressure is applied. For example, isopropylacetyl radical,

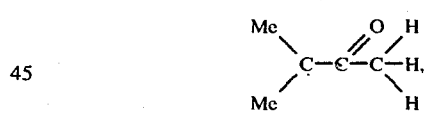

may be formed by dissolving manganic acetate in acetic acid in the presence of isopropyl methyl ketone; and as may be seen, the dangling valences of radical No. I are satisfied by methyl and hydrogen radicals. An enolizable ketone is one that undergoes enolization, as illustrated by equation (23) below.

The foregoing method of producing radicals by reacting a radical precursor compound with a manganic compound dissolved in acetic acid is applicable to the preparation of all the radicals listed in Table II, taking care, of course, to see that the proper radical precursor is present.

The ketone-derived radical No. II is formed from an enolizable ketone, or radical precursor, defined by the formula,

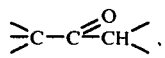

which includes such specific ketones as propyl isopropyl ketone,

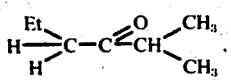

methyl isopropyl ketone,

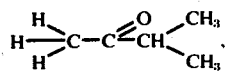

etc. It may be noted that unsymmetrical ketones give one or other of radicals Nos. I and II. To determine the particular radical, one may employ the following procedure in which, for illustrative purposes, an enolizable ketone like methyl n-propyl ketone,

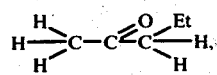

is used. Consider that the following reactions occur:

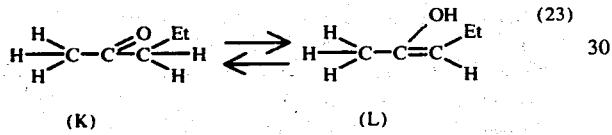
(K)   (L)      (23)

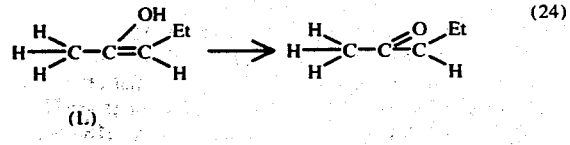
(L)            (24)

Equation (23) is the enolizing reaction by which the keto compound (K) forms the enol compound (L); the position of the double bond in (L) is determined by the number of H's on the carbons immediately next to (or alpha to) the carbonyl carbon, the double bond going to the carbon with the least H. Equation (24) is the radical-forming reaction; the selection of the free radical carbon is determined by two principles: it is the carbon (1) which participates in the double bond of enol compound (L) and (2) which is alpha to the hydroxyl-bearing carbon of enol compound (L).

A ketone, or radical precursor, like acetone, which has identical groups attached to the carbonyl carbon, produces a mixture of radicals,

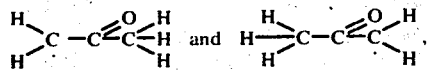

which represents types I and II of Table II, although in reality the same radical is involved; and this is true of other symmetrical ketones, such as diethyl ketone. Where the starting ketone is not symmetrical, one or other of types I and II tend to be formed, in accordance with the above discussion of equations (23) and (24). Some special cases exist, as with a ketone like

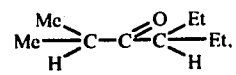

which, although not strictly symmetrical, has an enolizable H atom on each carbon alpha to the carbonyl carbon; it leads to mixtures of types I and II radicals. A special effect prevails in the case of a ketone like

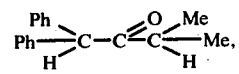

where the phenyl groups influence formation of radicals of type I; and in a ketone like

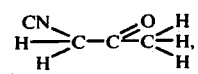

the cyano group influences formation of radicals of type I. These principles of radical type formation are known.

The aldehyde-derived radical No. III is formed from an enolizable aldehyde of the formula,

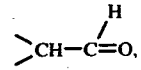

and this includes aldehydes like ethanal, propanal, butanal, buten-2-al, pentanal, pentenal, hendecanal, and other straight or branched chain aliphatic aldehydes having any desired number of carbons. An aromatic aldehyde like benzaldehyde or naphthaldehyde is excluded as it is not enolizable, but aldehydes like phenyl acetaldehyde, phenylpropionaldehyde, 2-pyridinepropionaldehyde, etc. are of use because they are enolizable. It will be recalled that enolizable aldehydes are capable of enolizing to form unsaturated alcohols.

Ester-derived radicals, note No. IV of Table II, are formed from enolizable esters corresponding to the formula,

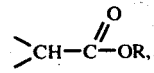

and including such esters as methyl acetate, methyl propionate, ethyl butyrate, and other aliphatic esters having any suitable number of carbons. Aromatic esters having an enolizable hydrogen atom are useful, such as alkyl esters of phenylacetic, phenylpropionic, coumaric, and other acids. Diesters such as malonic ester can also be employed. Enolizable esters are those containing an alpha hydrogen.

Nitrile-derived radicals, No. V of Table II, are formed from nitriles of the formula, >CH—CN, including such nitriles as acetonitrile, propionitrile, and any other acyl nitrile corresponding to such formula. Aromatic nitriles like benzonitrile are excluded, but compounds like phenylacetic acid nitrile, phenylpropionic acid nitrile and other such aryl-substituted alkanoic acid nitriles are within the formula.

Sulfoxide-derived radicals, Nos. VI and VII of Table II, are formed from enolizable sulfoxides corresponding to

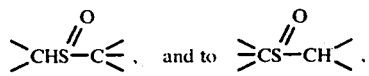

respectively. To determine which of radicals VI and VII is formed, one may apply the principles set forth in the discussion of equations (23) and (24). Thus, unsymmetrical sulfoxides like ethyl methyl sulfoxide,

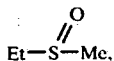

lead to type VI radical, while unsymmetrical sulfoxides like methyl propyl sulfoxide,

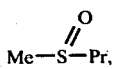

lead to type VII. A mixture of types VI and VII is obtained from symmetrical sulfoxides like dimethyl sulfoxide, diethyl sulfoxide, dipropyl sulfoxide, dibutyl sulfoxide, dibenzyl sulfoxide, etc. Non-enolizable sulfoxides like diphenyl sulfoxide, p-tolyl sulfoxide, etc., are not of use.

Radicals like No. VIII are derived from enolizable nitroparaffins of the general formula, $>CH-NO_2$, which includes nitromethane, nitroethane, nitropropanes, nitrobutanes, other nitroalkanes, and also nitrocycloparaffins like nitrocyclohexane and nitrocyclopentane. Also useful are enolizable alpha-nitrophenylalkanes and alpha-nitrodiphenylalkanes like alpha-nitrotoluene, alpha-nitrodiphenylmethane, etc.

Radical No. IX is derived from enolizable alkane thiosulfonic acid alkyl esters of the general formula, $>CH-SO_2SR$, where R is generally an alkyl group. Methane thiosulfonic acid methyl ester is an illustrative compound, and other useful compounds are those in which the methane moiety is substituted by any alkane or substituted-alkane moiety, and/or in which the methyl group is substituted by any alkyl group, provided that the resulting compound corresponds to the foregoing general formula.

Radical No. X is derived from enolizable alkanesulfonic acids of the formula, $>CH-SO_3H$, including compounds such as methanesulfonic acid, ethanesulfonic acid, and similar compounds in which the alkane moiety may be any desired alkane or substituted alkane group. For example, phenylmethanesulfonic acid, $PhCH_2-SO_3H$, is suitable, but a non-enolizable compound like benzenesulfonic acid is not.

Radical No. XI is derived from an alkanesulfinic acid of the formula, $>CH-SO_2H$, which includes methanesulfinic acid and other such acids having, in place of the methane moiety, any desired alkane moiety, including aryl-substituted alkane moieties like $PhCH_2-$, $Ph_2CH-$, and the like. However, an acid like toluenesulfinic acid, which is not enolizable, would not be suitable.

Thiyl radicals, No. XII of Table II, are derived from thiols (or mercaptans) of the general formula, HSR', where R' is a hydrocarbyl or substituted hydrocarbyl group. Suitable illustrative thiols include alkanethiols like methanethiol, ethanethiol, and any higher alkanethiol; arylthiols like benzenethiol, 2-naphthalenethiol; cycloalkanethiols like cyclohexanethiol, cyclohexanemethanethiol; alkarylthiols like benzenemethanethiol; aralkylthiols like toluenethiol, and the like. The group R' may also be equal to

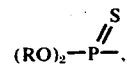

wherein the RO group is generally alkoxy, of which an exemplary thiol is O,O-dialkylthiophosphorothiol.

In the foregoing discussion of the radicals of Table II, it will be noted that the precursors of such radicals are designated by general formulas which involve dangling valences. These dangling valences may be satisfied by a wide variety of groups, including hydrogen, alkyl, aryl, alkaryl, aralkyl, acyl, aroyl, heterocyclic, chlorine, bromine, fluorine, nitrile, nitro, etc. These groups, of course, will also be present in the free radicals derived from the precursors. Of the various radicals listed in Table II, the preferred ones are Nos. I, II, III, IV, V, and XII, comprising the ketone-derived, aldehyde-derived, ester-derived, nitrile-derived, and thiyl radicals.

In the described manganic acetate/acetic acid method of preparing the various radicals, some variations are possible which may be noted briefly. Thus, in some cases the acetic acid solvent may be omitted where the free radical precursor has solvent power; for example, in preparing aldehyde-derived radicals, a precursor like acetaldehyde may be a sufficient solvent for the manganic acetate; also, nitrile radical precursors, such as acetonitrile, may dissolve the manganic acetate, particularly at higher temperatures; in the preparation of thiyl radicals, thiol precursors are frequently good enough solvents; and precursors like the sulfoxides, alkanesulfonic acids, and alkanesulfinic acids are good solvents for the manganic acetate and may eliminate need for using acetic acid or other solvent, although the latter may be added if desired.

The preferred metal ion for the olefin/free radical addition reaction is trivalent manganese, or manganic ion $Mn^{+3}$, which, as indicated above, is reducible during the reaction to bivalent manganese, or manganous ion $Mn^{+2}$. As shown by equations (1) – (5), the $Mn^{+3}$, and the manganic acetate which provides it, can be reactants. Manganic acetate dihydrate is a preferred $Mn^{+3}$-producing compound; it may be formed by oxidizing an acetic acid solution of manganous acetate with potassium permanganate. Other suitable $Mn^{+3}$-producing source compounds or mixtures include anhydrous manganic acetate; also a mixture of activated (i.e., freshly prepared or acid treated) manganese dioxide and acetic acid; a mixture of manganese sesquioxide and acetic acid; and a mixture of $Mn_3O_4$ and acetic acid. Also a solution of manganese chloride and acetic acid; or manganese fluoride, or manganic hypophosphate dihydrate, or manganic sulfate, or manganic phosphate monohydrate, or manganic pyrophosphate, or manganic propionate, each dissolved in acetic acid or one of the solvents noted below. Other higher-valent manganese ions, in solution, may be of use, such as $Mn^{+4}$, as obtained from a mixture of $MnO_2$ and acetic acid; also $Mn^{+6}$, as supplied by the manganate of sodium, potassium, ammonium, lithium, magnesium, strontium, calcium or barium, etc.; also $Mn^{+7}$, as supplied by the permanganate of sodium, ammonium, potassium, or magnesium, etc. Whatever higher-valent manganese ion-supplying compound is chosen, it should be soluble in the solvent as described below. In addition to the foregoing higher-valent manganese ions, it is feasible to employ mixtures of ions, such as $Mn^{+2}$ plus any of $Mn^{+3}$, $Mn^{+4}$, $Mn^{+6}$, or $Mn^{+7}$; or $Mn^{+3}$ plus any of $Mn^{+4}$, $Mn^{+6}$, or $Mn^{+7}$; or $Mn^{+4}$ plus $Mn^{+6}$ or $Mn^{+7}$; or $Mn^{+6}$ plus $Mn^{+7}$. Such mixtures may be supplied by suitable mixtures of the foregoing source compounds. The $Mn^{+2}$ ion may be supplied by any soluble manganous compound, such as the acetate, propionate, nitrate, oxide, hydroxide, chloride, sulfate, phosphate, perchlorate, etc.

The manganese source compound may be added per se to the reaction mixture, or if desired it may be formed in situ. In situ formation may suitably be performed by adding to the reaction mixture a manganous compound like manganous acetate together with a solvent therefor like acetic acid and also adding an oxidizing agent so that the $Mn^{+2}$ ion is oxidized at least to $Mn^{+3}$ ion. Other manganous compounds include those named in the preceding paragraph, and other solvents include alkali metal acetates and carbonates as well as those described below. Suitable oxidizing agents include nitric acid, potassium permanganate, chlorine, oxygen, air, potassium manganate, cerium ammonium nitrate, cobaltic acetate, various peroxides like paracetic acid and hydrogen peroxide, or intermediates peroxides or hydroperoxides resulting from the air oxidation of hydrocarbons. Electrochemical oxidation is a suitable oxidizing procedure.

Besides manganese, cerium and vanadium are of use in the reaction. Each of these metal ions has at least two valency states, a lower and a higher, above the zero valent form of the metal. Thus, manganese has valency states of 2, 3, 4, 6, and 7, cerium has valency states of 3 and 4, and vanadium has valency states of 2, 3, 4, and 5. Each is available, in a higher-valent state, as the acetate, or other suitable compound, which is decomposable under the conditions of the reaction to give a metal ion of lower valence. In their higher valency states, these metal ions have a relatively good oxidation potential, and in their lower valency states, they tend to be stable and reoxidizable to the higher valency states.

As mentioned, a solvent can be employed. In this connection, the product of the reaction can, in some instances, reflect the anion of the metal compound or the solvent, or both the anion of the metal compound and the solvent, used in the reaction. For example, in equation (4), where manganic acetate dissolved in acetic acid is employed, the product (P-1) contains an acetoxy group reflecting the anion of the manganic acetate and of the acetic acid. If propionic acid were employed as the solvent instead of acetic acid, the propionate group of the solvent, as well as the acetate group of the manganic acetate, would be reflected in the product. Thus, some of the product (P-1) would contain an acetoxy group and some would contain a propionoxy group. The relative proportion of the product (P-1) containing the acetoxy group and the propionoxy group will depend upon the relative proportions of the acetate anion and the propionate anion in the reaction mixture. If the metal compound is manganese sesquioxide and the solvent is an aqueous solution of acetic acid, the product will have a hydroxy group instead of an acetoxy group owing to the effect of the water in the solvent. Also, if the metal compound is manganic acetate and the solvent is water, the product will have a hydroxy group instead of an acetoxy group. In general, if water is present in the reaction mixture, the product will have the described hydroxy group.

With respect to the solvent, where the anion of the metal salt providing the metal enters into the reaction and the product reflects the anion of the metal compound, and this product is the desired product, a nonpolar solvent can be employed. Alternatively, a polar solvent can be employed. However, in this instance, the anion of the polar solvent must be the same as that of the metal salt.

Further with respect to the solvent, where the anion of the metal salt does not enter into the reaction and the product does not reflect the anion of the metal compound, either a polar or non-polar solvent may be employed.

Useful solvents are glacial acetic acid, or glacial acetic acid plus water, or glacial acetic acid plus a paraffinic hydrocarbon in varying amounts, the latter suitably having 6 to 16 carbons. Propionic and butanoic acids are also preferred solvents, and also of use are alkanoic acids having up to 20 or 30 carbons. Anhydrides of the foregoing acids, ranging from acetic acid anhydride to the anhydride of C-20 or C-30 acids, are suitable for use as solvents. Esters of these acids are useful solvents, and also aliphatic ethers having up to 20 or 30 carbons and aliphatic hydrocarbons of the same carbon atom range. Water can be employed as a solvent. Frequently the foregoing solvents dissolve not only the metal compound but also the unsaturated compound; although it will be understood that a separate solvent, such as an alkane, can be used for the latter and that it will be miscible with the first-mentioned solvent.

Considering now the conduct of the reaction, the concentration of the olefin may range from 0.01 to 5 moles, preferably 0.25 to 1 mole, per mole of manganic or other higher-valent metal compound. The free radical precursor is preferably present in an amount to provide one free radical per molecule of olefin. The solvent, such as acetic acid, should be present in an amount sufficient to dissolve the olefin and the metal compounds. The reaction is suitably performed by refluxing the foregoing components, although lower temperatures may be used, ranging from about 40° to 100° C. Temperatures above boiling are of use but in this case the reaction is performed under pressure to maintain a liquid phase. Reaction times generally extend from an hour or less to 5 or 10 hours or more. An inert atmosphere, such as one of nitrogen, carbon dioxide, helium, and the like is desirably maintained over the reaction mixture to lessen or avoid oxidation by air.

At the conclusion of the reaction, separation of the product may be effected as by conventional distillation, extraction, fractional crystallization, and the like with or without the aid of conventional filtration or centrifugation. For example, in a reaction mixture containing the product, acetic acid, reduced manganous salt like manganous acetate, and any unreacted olefin, the mixture may be filtered to remove any solids and then subjected to distillation, using vacuum if necessary to separate the product from other components. Or the reaction mixture may be mixed with additional quantities of acetic acid sufficient to dissolve all the manganous acetate and the resulting mixture distilled under vacuum to isolate the product; in this case the manganese salt may be found in the column bottoms.

As indicated, high yields of product are obtainable. Up to 95%, or more, of the olefin may be converted to product, indicating that the X free radical has very good selectivity to addition to the multiple bond in the presence of the described metal ion. On the basis of manganese reduced, about 1 mole of product may be formed per 2 moles of manganese compound reduced. The addition of anhydrous potassium acetate, or other alkali metal acetate, when manganic acetate and acetic acid are used, may help to suppress formation of minor side products; this same effect may also be favored in some cases by using lower concentrations at the lower end of the above-described ranges.

The manganous compound that is formed as a consequence of the reduction of the manganic compound may, as already indicated, be saved and used to regenerate the manganic compound. Thus, where the manganous compound is manganous acetate, it is desirably isolated from the reaction mixture, heated at 200°–300° C. to form MnO, acetone, and carbon dioxide, and the MnO then heated in air or oxygen to form $MnO_2$, $Mn_2O_3$, and/or $Mn_3O_4$. On dissolving these oxides in acetic acid, there is formed manganic acetate, and this solution is of use to prepare a product in accordance, say, with equations (1) through (5) above. The acetone, of course, is valuable enough to recover.

Alternatively, the isolated manganous acetate may be dissolved in acetic acid and the solution electrolyzed, using a carbon or other suitable anode, to form manganic acetate, the resulting electrolyzed solution being directly usable in a free radical reaction. Where the manganous acetate is already in solution in acetic acid, no preliminary isolation step is necessary as such solution may be charged to the electrolysis cell and electrolyzed.

Or the isolated manganous acetate may be dissolved in water, the solution buffered to pH 6 to 8 by means of ammonium chloride or other suitable buffer, and air or oxygen passed through the solution to produce manganese sesquioxide. This oxide is filtered and dissolved in acetic acid to form a solution of manganic acetate.

The isolated manganous acetate may also be treated with an oxidizing agent like concentrated or fuming nitric acid plus acetic anhydride to produce anhydrous manganic acetate, which is useful per se in the free radical reaction.

As a further alternative, the manganous acetate, either isolated or in acetic acid solution, may be mixed with acetic acid and with activated $MnO_2$ to form manganic acetate. To obtain activated $MnO_2$, one can freshly prepare this oxide, or can treat an existing sample with a dilute mineral acid following this with water washing and drying.

Manganous acetate can also be oxidized to manganic acetate by treatment with potassium permanganate.

The foregoing regeneration procedures generally apply to other manganous compounds besides the acetate; and with suitable modifications they are applicable to the regeneration of other higher-valent cerium and vanadium compounds from lower-valent forms thereof. It will be appreciated that the regeneration step permits the manganese compound, or other metal compound, to be used over and over and therefore represents a significant economy.

The following examples will be illustrative of the invention.

EXAMPLE 1

About 17 grams (g.) (0.06 mole (m.)) of manganic acetate, $Mn(OCOCH_3)_3 \cdot 2H_2O$, were added to a flask containing 10 g. of potassium acetate and 100 milliliters (ml.) of acetic aicd, after which the flask contents were heated on an oil bath at 70° C., using stirring and a nitrogen purge. When the manganese had dissolved, a mixture of 220 ml. of acetone (3.0 m.) and 5.6 g. (0.05 m..) of octene-1 was added and heating continued until the brown color of $Mn^{+3}$ disappeared, indicating completion of the reaction. The mixture was cooled, diluted with ice water, and extracted with ether. The ether extract was washed with water and sodium bicarbonate, and the ether removed. The resulting products comprised a keto-ester,

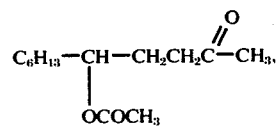

or 5-acetoxy-undecanone-2, b.p. 104°–116° C. at 1.0 millimeters (mm.) mercury, yield 19%, and an unsaturated ketone,

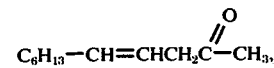

or undecen-4-one-2, b.p. 79°–81° C. at 1.5 mm. mercury, yield 6%. Yields are based on manganese consumed. Under other reaction conditions, a third product, namely, undecanone-2, is obtained.

EXAMPLE 2

About 126 g. (0.44 m.) of manganic acetate were added to a mixture of 350 ml. of acetic acid and 35 g. of potassium acetate in a flask and stirred over low heat, using a nitrogen purge, until the manganese compound dissolved. To the mixture there were added 139.4 g. (2.4 m.) of acetone and 22.9 g. (0.22 m.) of styrene, and reaction was continued until the brown $Mn^{+3}$ color was gone. The maximum temperature was about 75° C. and the reaction required about 30 minutes. The mixture was cooled and worked up as in Example 1 Two products were identified:

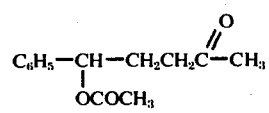

or 5-acetoxy-5-phenyl-pentanone-2, b.p. 105° C. at 0.1 mm. mercury, yield 27%, and

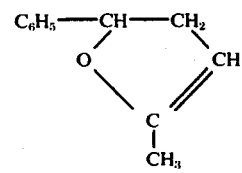

or 1-phenyl-4-methyl-dihydrofuran, b.p. 77° C at 0.4 mm. mercury, yield 14%. Yields are based on Mn$^{+3}$ consumed.

EXAMPLES 3 – 5

Using substantially the same procedure as in Examples 1 and 2, the following reactions were run, involving (3) dodecene-1 plus acetone, (4) octene-1 plus acetophenone, and (5) styrene plus acetophenone:

| No. | Olefin | Radical Derived From | Products |
|---|---|---|---|
| 3 | Dodecene-1 | Acetone | 5-acetoxy-pentadecan-2-one plus pentadecen-4-one-2 |
| 4 | Octene-1 | Acetophenone | Gamma-acetoxy-nonanophenone plus 2-nonenophenone |
| 5 | Styrene | Acetophenone | 4-acetoxy-4-phenyl-butyrophenone plus 1,4-diphenyl-dihydrofuran |

EXAMPLE 6

To a solution of manganic acetate in acetic acid, prepared in situ by the addition of 16 g. of potassium permanganate (0.1 m.) to 88 g. of manganous acetate dihydrate (Mn(OAc)$_2$·2H$_2$O) (0.42 m.) in 570 milliliters of glacial acetic acid followed by 124 ml. of acetic anhydride and 60 g. of potassium acetate, were added 100 g. (1.0 m.) of isopropenyl acetate and 98 g. (1.0 m.) of cyclohexanone. The reaction mixture was heated under nitrogen to 70° C. until the brown manganic color disappeared. The reaction mixture was cooled, diluted with water, and extracted with ether. The product, 2-acetonyl-cyclohexanone

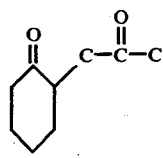

was isolated by distillation, b.p. 70° C. at 0.05 mm. mercury, yield about 8 g. (20% based on Mn).

EXAMPLE 7

Same as Example 6, except that acetophenone was used in place of cyclohexanone. The product, 1-phenyl-pentandione-1,4 (b.p. 105° C. at .1 mm. mercury) was obtained in 20% yield based on Mn.

EXAMPLE 8

Same as Example 6, except that 3-methylheptanone-2 was used in place of cyclohexanone. The major product isolated was 6-methyldecadione-2,5 in 17% yield based on Mn.

EXAMPLE 9

Same as Example 6, except that octanone-2 was used in place of cyclohexanone. Two isometric diones were obtained in 30% yield based on Mn. The major isomer was

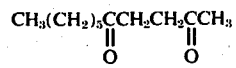

and minor product was

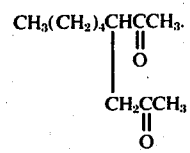

EXAMPLE 10

Same as Example 6, except the 2-methylcyclohexanone was used in place of cyclohexanone. The products obtained in 20% yield based on Mn consisted of cis and trans

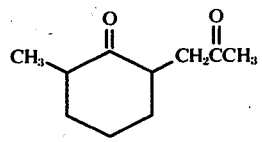

as the major products together with some minor amounts of

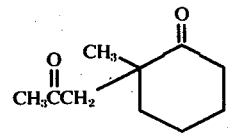

EXAMPLE 11

Same as Example 6, except that vinyl acetate was used in place of isopropenyl acetate. The expected product, an aldehyde,

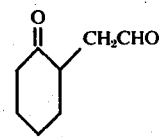

was obtained.

EXAMPLE 12

Same as Example 11, except that vinyl isobutyl ether was used in place of vinyl acetate. The identical aldehyde product was obtained.

EXAMPLE 13

Same as Example 6, except that butyraldehyde was used in place of cyclohexanone. The 4-keto aldehyde

was obtained as the major product.

EXAMPLE 14

Same as Example 6, except that dimethylmalonate was used in place of cyclohexanone. The 4-keto-diester,

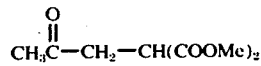

was obtained in 22% yield based on Mn. This product was converted in high yield to levulinic acid

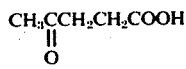

by acid hydrolysis.

Examples 15–21 will illustrate the preparation of dihydrofurans.

EXAMPLE 15

The procedure of Example 1 was repeated except that the ketone was

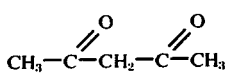

and the olefin was

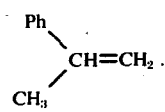

The product,

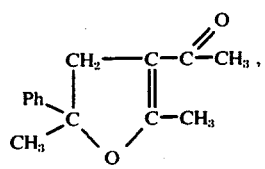

was obtained in a yield of 100%. This yield, similar to the yields in Examples 16–21, is based upon the $Mn^{+++}$ consumed, assuming 2 equivalents per mole of product.

EXAMPLE 16

Same as Example 15 except that the olefin was $PhCH=CH_2$. A product,

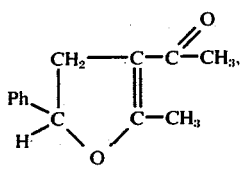

was obtained in a yield of 30%.

EXAMPLE 17

Same as Example 15 except that the olefin was

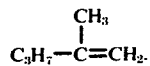

A product,

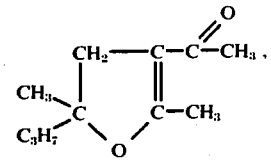

was obtained in a yield of 40%.

EXAMPLE 18

Same as Example 15 except that the olefin was $C_6H_{13}CH=CH_2$. A product,

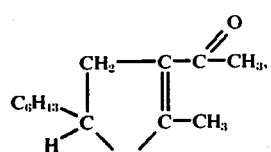

was obtained in a yield of 10%. The yield of the product was 33% in the presence of trifluoroacetic acid as cosolvent.

EXAMPLE 19

Same as Example 1 except that the ketone was

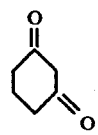

and the olefin was

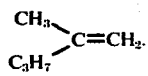

A product,

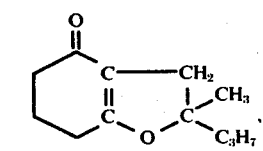

was obtained in a yield of 74%.

EXAMPLE 20

Same as Example 19 except that the olefin was

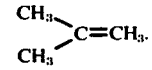

A product,

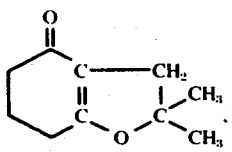

was obtained in a yield of about 40%.

EXAMPLE 21

Same as Example 1 except that the ketone was

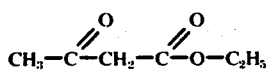

and the olefin was Ph-CH=CH$_2$. A product,

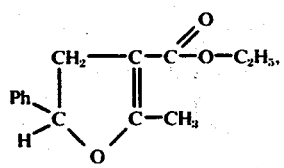

was obtained in a yield of 57%.

EXAMPLE 22

The procedure of Example 6 was followed except that the olefin was diallylsulfide. A product,

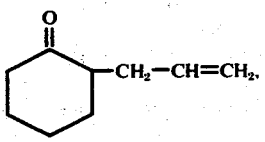

was obtained in a yield of 0.3 moles per mole of manganic ion.

EXAMPLE 23

Same as Example 22 except that the olefin was phenyl allyl sulfide. The same product in the same yield as in Example 22 was obtained.

EXAMPLE 24

Same as Example 6 except that the olefin was methallyl chloride. A product,

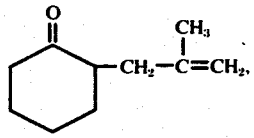

was obtained in a yield of 0.4 mole per mole of manganic ion.

EXAMPLE 25

Same as Example 6 except that the olefin was 3-chlorobutene-1. A product,

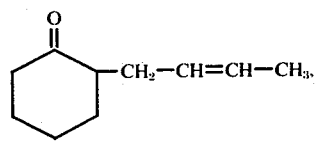

was obtained in a yield of 0.4 mole per mole of manganic ion.

EXAMPLE 26

A solution of 9.0 g. of 2-methyl-1-propanethiol in 90 ml. acetic acid (HOAc) was added dropwise to a solution of 20.8 g. of styrene in one liter of HOAc containing 1 mole of potassium acetate and 0.1 mole of manganic acetate. When addition was completed and the brown color of manganic ion had disappeared, the reaction mixture was extracted with ether and stripped. The product was obtained by distillation as a liquid, b.p. approximately 100° C. at 0.02 mm. mercury, and was identified as the acetate

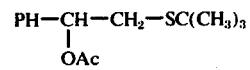

by analytical and spectral means.

EXAMPLE 27

Same as Example 26 except alpha-methylstyrene was used in place of styrene.

The products obtained by the process of the invention have various utilities. Thus, for example, the keto-esters are of value as additives for improving the octane rating of leaded gasoline fuels. The keto-esters can also be hydrolyzed to form the corresponding acids which can be employed for improving the octane rating of gasolines. The keto-esters such as (P-1) where R'' is hydrogen can be reduced and hydrolyzed to 1,4-butanediol which can be used for preparing varnishes and self-polishing wax emulsions or as an ingredient of a solution for nickel plating. Diesters such as (P-11) where R is hydrogen can be partially reduced to form gamma-hydroxybutyric acid whose lithium, sodium and potassium salts can be used as a grease component. Where R is C$_7$H$_{15}$, acid treatment converts the compound to a lactone which can be used as a flavoring agent. Cyano-esters such as (P-13) where R'' is hydrogen can be reduced to 1,4-butanolamine which can be used as a non-aqueous organic electrolyte, especially for capacitors, or can be reduced to form gamma-hydroxybutyronitrile and the latter hydrolyzed to form butyrolactone which has utility as a solvent, for example, for polyacrylonitrile. An acetoxy-substituted nitropropane, such as (P-19), where R'' is hydrogen can be hydrolyzed to form 3-nitro-1-hydroxypropane which can be employed in the preparation of polynitrated compounds. The sultones such as (P-23) can be used as an antistatic and a hardener in plastics. The dihydrofuran derivatives such as I, II, and III, can be converted to the corresponding carbamates which have pesticidal activity. The products obtained from alkanesulfinic and alkanesulfonic acids and their sodium, calcium, barium, and lithium salts are oil additives for passenger car lubricants and as detergents. The corresponding esters, sulfones, and sulfoxides are load carrying agents for gear oil. The products obtained from ketones, aldehydes, and esters can be converted to the corresponding acids by conventional techniques to produce edible fatty acids, glycerides, and water-soluble or oil-soluble soaps depending upon the number of carbon atoms. The products obtained from nitroparaffins can be used as such as cetane improvers.

In light of the foregoing description, the following is claimed.

We claim:

1. Method of selectively reacting a free radical X with an olefin, said free radical X being selected from the group consisting of

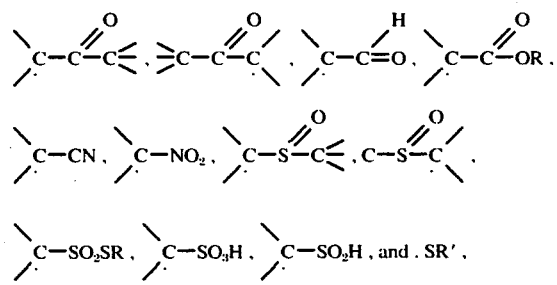

Where R is an alkyl group and R' is a hydrocarbyl or substituted hydrocarbyl group, and said free radical being derived respectively from a ketone, a ketone, an aldehyde, an ester, a nitrile, a nitroparaffin, a sulfoxide, a sulfoxide, a thiosulfonic acid ester, an alkanesulfonic acid, an alkanesulfinic acid, and a thiol, comprising reacting said olefin, a compound selected from the group consisting of ketones, aldehydes, esters, nitriles, sulfoxides, nitroparaffins, thiosulfonic acid esters, alkanesulfonic acids, allkanesulfinic acids, and thiols, and a stoichiometric quantity of an ion of manganese, vanadium, or cerium having a valence higher than the lowest valence above the zero valent form of the metal to form a product containing the structure

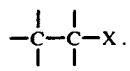

2. Method of claim 1 wherein said olefin has one double bond.

3. Method of claim 2 wherein said olefin has the formula

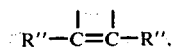

where R'' is a group selected from hydrogen, alkyl, alkenyl, alkynyl, aryl, alkaryl, aralkyl, acyl, acyloxy, alkoxy, alkyl sulfide, aldehyde, alkyl aldehyde, amide, alkyl amide, aryloxy, aroyl, aroyloxy, carboxyl, alkyl carboxyl, alkenyl carboxyl, cyanide, alkyl cyanide, alkenyl cyanide, halogen, mercapto, alkyl mercapto, aryl mercapto, alkenyl mercapto, aralkyl mercapto, alkaryl mercapto, isocyanide, nitro, and heterocyclic groups, each R'' is the same as or different from the other R'', and wherein the dangling valences in said formula may be satisfied by groups that are the same as or different from R'' and are selected from the foregoing groups.

4. Method of claim 3 wherein said R'' groups are organyl groups that are the same or different.

5. Method of claim 3 wherein said R'' groups are hydrocarbyl groups that are the same or different.

6. Method of claim 3 wherein said R'' groups are hydrocarbyl-containing groups that are the same or different.

7. Method of claim 3 wherein said olefin has one double bond.

8. Method of claim 1 wherein said ion is added to the reaction mixture in the form of a compound of a higher-valent form of said metal.

9. Method of claim 1 wherein said ion of higher-valent form is produced in situ in the reaction mixture from a compound of the metal of lower-valent form.

10. Method of claim 1 wherein said ion is a manganese ion.

11. Method of claim 10 wherein said manganese ion is $Mn^{+3}$.

12. Method of claim 1 wherein said ion is a cerium ion.

13. Method of claim 1 wherein X is a carbonyl-containing radical selected from

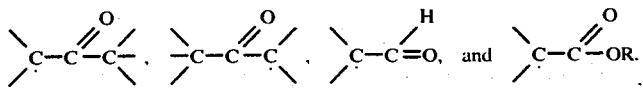

14. Method of claim 1 wherein X is a sulfur-containing radical selected from

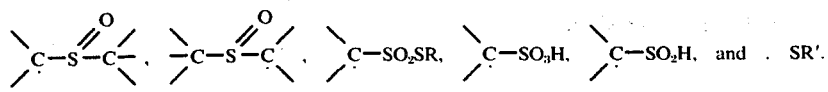

15. Method of claim 1 wherein X is an oxy-sulfur-substituted methyl radical selected from

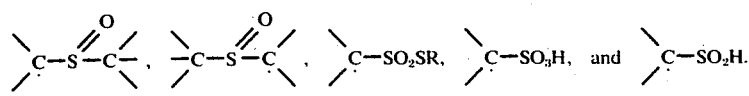

16. Method of claim 1 wherein X is a nitrogen-containing radical selected from >C-CN and >C-NO$_2$.

17. Method of claim 1 wherein X is

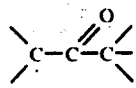

18. Method of claim 1 wherein X is

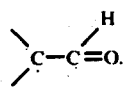

19. Method of claim 1 wherein X is

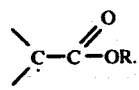

20. Method of claim 1 wherein X is >C-CN.
21. Method of claim 1 wherein X is

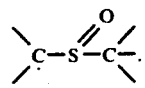

22. Method of claim 1 wherein X is

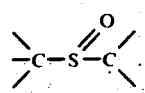

23. Method of claim 1 wherein X is >C-NO$_2$.
24. Method of claim 1 wherein X is >C-SO$_2$SR.
25. Method of claim 1 wherein X is >C-SO$_3$H.
26. Method of claim 1 wherein X is >C-SO$_2$H.
27. Method of claim 1 wherein X is ·SR'.
28. Method of reacting a free radical ·X with an olefin comprising heating said olefin with a source of said free radical ·X in the presence of a stoichiometric amount of manganic acetate and in the presence of acetic acid for a time sufficient to form an addition product comprising said olefin and said free radical, said free radical ·X being selected from the group consisting of

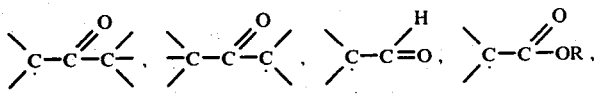

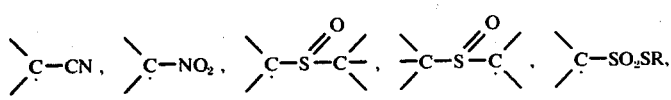

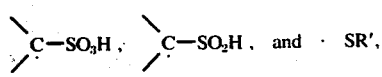

where R is an alkyl group, and R' is a hydrocarbyl or substituted hydrocarbyl group, said free radical being derived respectively from a ketone, a ketone, an aldehyde, an ester, a nitrile, a nitorparaffin, a sulfoxide, a sulfoxide, a thiosulfonic acid ester, an alkanesulfonic acid, an alkanesulfinic acid, and a thiol.

29. Method of selectively reacting a free radical ·X with an olefin, said free radical ·X being selected from the group consisting of

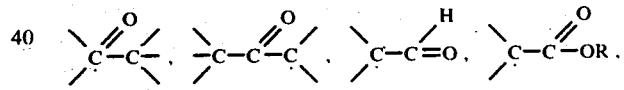

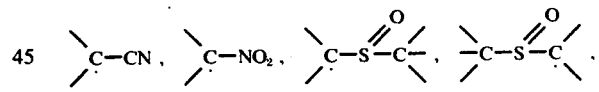

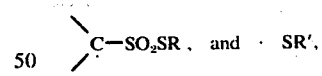

where R is an alkyl group and R' is a hydrocarbyl or substituted hydrocarbyl group, and said free radical being derived respectively from a ketone, a ketone, an aldehyde, an ester, a nitrile, a nitroparaffin, a sulfoxide, a sulfoxide a thiosulfonic acid ester, and a thiol, comprising reacting said olefin with a compound selected from the group consisting of ketones, aldehydes, esters, nitriles, sulfoxides, nitroparaffins, thiosulfonic acid esters, and thiols, in the presence of a stoichiometric amount of an ion of manganese, vanadium, or cerium having a valence higher than the lowest valence above the zero valent form of the metal to form a product containing the structure,

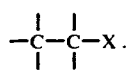

30. Method of selectively reacting a free radical ·X with an olefin, said free radical ·X being selected from the group consisting of >C-SO₃H and >CSO₂H, and said free radical being derived respectively from an alkanesulfonic acid and an alkanesulfinic acid, comprising reacting said olefin with a compound selected from the group consisting of alkanesulfonic acids and alkanesulfinic acids, in the presence of a stoichiometric amount of an ion of manganese, vanadium, or cerium having a valence higher than the lowest valence above the zero valent form of the metal to form a product containing the structure,

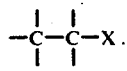

31. Method of claim 1 wherein said ion is a vanadium ion.

32. Method of claim 17 wherein said olefin is an octene.

33. Method of claim 32 wherein said ion is a manganese ion.

34. Method of claim 32 wherein said ion is a cerium ion.

35. Method of claim 32 wherein said ion is a vanadium ion.

36. Method of reacting a free radical ·X with an olefin comprising heating said olefin with a source of said free radical ·X in the presence of a stoichiometric amount of manganic propionate and in the presence of propionic acid for a time sufficient to form an addition product comprising said olefin and said free radical, said free radical ·X being selected from the group consisting of

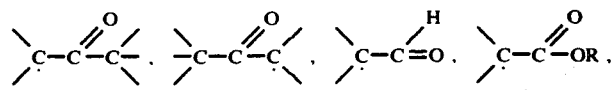

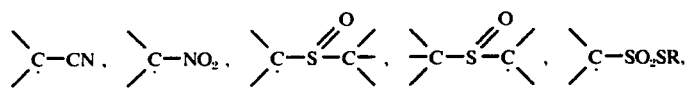

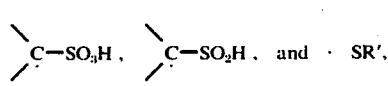

where R is an alkyl group, and R' is a hydrocarbyl or substituted hydrocarbyl group, said free radical being derived respectively from a ketone, a ketone, an aldehyde, an ester, a nitrile, a nitroparaffin, a sulfoxide, a sulfoxide, a thiosulfonic acid ester, an alkanesulfonic acid, an alkanesulfinic acid, and a thiol.

37. Method of reacting a free radical,

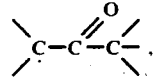

derived from a ketone with an octene comprising heating said ketone and said octene in the presence of a stoichiometric amount of manganic acetate and in the presence of acetic acid for a time sufficient to form an unsaturated ketone product of said octene and said free radical and a keto-ester product of said octene, said free radical, and the acetate portion of said manganic acetate.

38. Method of claim 1 wherein said free radical ·X is

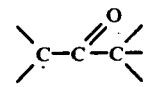

derived from a ketone, said olefin is an enol ester, and said product is a diketone.

39. Method of claim 1 wherein said free radical ·X is

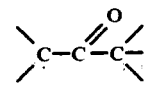

derived from a ketone, said olefin is an enol ether, and said product is a diketone.

40. Method of claim 1 wherein said free radical ·X is

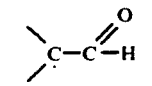

derived from an aldehyde, said olefin is an enol ether, and said product is a keto-aldehyde.

41. Method of claim 1 wherein said free radical ·X is

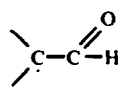

derived from an aldehyde, said olefin is an enol ester, and said product is a keto-aldehyde.

42. Method of claim 1 wherein said free radical ·X is

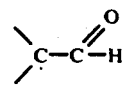

derived from an aldehyde, said olefin is a vinyl ester, and said product is a keto-aldehyde.

43. Method of claim 1 wherein said free radical ·X is

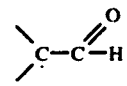

derived from an aldehyde, said olefin is a vinyl ester, and said product is a keto-aldehyde.

44. Method of claim 1 wherein said free radical ·X is

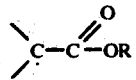

derived from an ester, said olefin is an enol ester, and said product is a keto-ester.

45. Method of claim 1 wherein said free radical ·X is

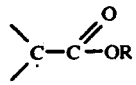

derived from an ester, said olefin is an enol ether, and said product is a keto-ester.

46. Method of claim 1 wherein said free radical ·X is

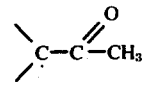

derived from a ketone, said olefin is an aryl substituted olefin, and said product is a dihydrofuran.

47. Method of claim 46 wherein said ketone is a diketone.

48. Method of claim 47 wherein said diketone is a cyclic diketone.

49. Method of claim 48 wherein said diketone is a non-cyclic diketone.

50. Method of claim 48 wherein said cyclic diketone is 1,3-cyclo-hexanedione.

51. Method of claim 49 wherein said non-cyclic diketone is 2,4-pentanedione.

52. Method of claim 46 wherein said ketone is a beta-keto-ester.

53. Method of claim 46 wherein said ketone is a beta-keto-nitrile.

54. Method of claim 46 wherein said ketone is a beta-keto-amide.

55. The method of claim 1 wherein said free radical ·X is

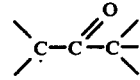

derived from a diketone and said product is a dihydrofuran.

56. The method of claim 55 wherein said olefin is an aryl-substituted olefin.

57. The method of claim 1 wherein said free radical ·X is

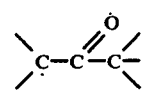

derived from a cyclic ketone and said olefin is an allyl chloride or sulfide.

58. The method of claim 1 wherein said free radical ·X is

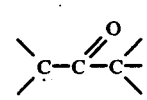

derived from a ketone and said olefin is an allyl chloride or sulfide.

* * * * *